(12) United States Patent
Krishna et al.

(10) Patent No.: US 8,490,474 B2
(45) Date of Patent: Jul. 23, 2013

(54) METHODS, SYSTEMS AND APPARATUS FOR DETECTING MATERIAL DEFECTS IN COMBUSTORS OF COMBUSTION TURBINE ENGINES

(75) Inventors: Pradeep Aadi Gopala Krishna, Karnataka (IN); Dullal Ghosh, Orissa (IN); Saurav Dugar, West Bengal (IN); Matthew Paul Berkebile, Mauldin, SC (US); Anthony Wayne Krull, Anderson, SC (US)

(73) Assignee: General Electric Company, Schenectady, NY (US)

( * ) Notice: Subject to any disclaimer, the term of this patent is extended or adjusted under 35 U.S.C. 154(b) by 391 days.

(21) Appl. No.: 12/981,898

(22) Filed: Dec. 30, 2010

(65) Prior Publication Data

US 2012/0167664 A1 Jul. 5, 2012

(51) Int. Cl.
*G01M 15/00* (2006.01)
*G01N 19/00* (2006.01)
*F01B 25/26* (2006.01)

(52) U.S. Cl.
USPC ............... 73/112.01; 73/865.9; 415/118

(58) Field of Classification Search
USPC ............ 73/23.4, 86, 112.01, 865.9; 116/207, 116/216; 137/551; 138/104; 415/118
See application file for complete search history.

(56) References Cited

U.S. PATENT DOCUMENTS

| 5,865,598 | A | * | 2/1999 | Twerdochlib | ............ | 415/118 |
| 6,200,088 | B1 | * | 3/2001 | Zombo et al. | ............ | 415/118 |
| 6,278,374 | B1 | | 8/2001 | Ganeshan | | |
| 6,512,379 | B2 | | 1/2003 | Harrold et al. | | |
| 6,644,917 | B2 | * | 11/2003 | Zhao et al. | ............ | 415/200 |
| 7,052,737 | B2 | * | 5/2006 | Kool et al. | ............ | 427/256 |
| 7,123,031 | B2 | | 10/2006 | Twerdochlib | | |
| 2006/0088793 | A1 | | 4/2006 | Brummel et al. | | |

\* cited by examiner

*Primary Examiner* — Hezron E Williams
*Assistant Examiner* — Nathaniel Kolb
(74) *Attorney, Agent, or Firm* — Mark E. Henderson; Ernest G. Cusick; Frank A. Landgraff

(57) ABSTRACT

A system for detecting defects in a combustion duct of a combustion system of a combustion turbine engine while the combustion turbine engine operates, wherein the combustion duct comprises a hot side, which is exposed to combustion gases and, opposing the hot side, a cold side. The system may include: an indicator coating disposed on an outer surface of the combustion duct, the indicator coating comprising a detectable substance; and a gas sensor positioned downstream of the combustor, the gas sensor configured to take a measurement of the amount of the detectable substance in the combustion products of the combustion turbine engine.

24 Claims, 11 Drawing Sheets

METHODS, SYSTEMS AND APPARATUS FOR DETECTING MATERIAL DEFECTS IN COMBUSTORS OF COMBUSTION TURBINE ENGINES

BACKGROUND OF THE INVENTION

This present application relates generally to methods, systems, and apparatus for detecting defects, including surface defects, which may occur in industrial manufacturing processes, engines, or similar systems. More specifically, but not by way of limitation, the present application relates to methods, systems, and apparatus pertaining to the detection of defects that form on the components, such as those found within the combustor, exposed to the hot-gases of combustion turbine engines.

In operation, generally, a combustion turbine engine may combust a fuel with compressed air supplied by a compressor. As used herein and unless specifically stated otherwise, a combustion turbine engine is meant to include all types of turbine or rotary combustion engines, including gas turbine engines, aircraft engines, etc. The resulting flow of hot gases, which typically is referred to as the working fluid, is expanded through the turbine section of the engine. The interaction of the working fluid with the rotor blades of the turbine section induces rotation in the turbine shaft. In this manner, the energy contained in the fuel is converted into the mechanical energy of the rotating shaft, which, for example, then may be used to rotate the rotor blades of the compressor, such that the supply of compressed air needed for combustion is produced, and the coils of a generator, such that electrical power is generated. During operation, it will be appreciated that components exposed to the hot-gas path become highly stressed with extreme mechanical and thermal loads. This is due to the extreme temperatures and velocity of the working fluid, as well as the rotational velocity of the turbine. As higher firing temperatures correspond to more efficient heat engines, technology is ever pushing the limits of the materials used in these applications.

Whether due to extreme temperature, mechanical loading or combination of both, component failure remains a significant concern in combustion turbine engines. A majority of failures can be traced to material fatigue, which typically is forewarned by the onset of crack propagation. More specifically, the formation of cracks caused by material fatigue remains a primary indicator that a component has reached the limit of its useful life and may be nearing failure. The ability to detect the formation of cracks remains an important industry objective, particularly when considering the catastrophic damage that the failure of a single component may occasion. Such a failure event may cause a chain reaction that destroys downstream systems and components, which require expensive repairs and lengthy forced outages.

One manner in which the useful life of hot-gas path components may be extended is through the use of protective coatings, such as thermal barrier coatings. In general, exposed surfaces are covered with these coatings, and the coatings insulate the component against the most extreme temperatures of the hot-gas path. However, as one of ordinary skill in the art will appreciate, these types of coatings wear or fragment during usage, a process that is typically referred to as "coating spallation" or "spallation". Spallation may result in the formation and growth of uncoated or exposed areas at discrete areas or patches on the surface of the affected component. These unprotected areas experience higher temperatures and, thus, are subject to more rapid deterioration, including the premature formation of fatigue cracks and other defects. In combustion turbine engines, coating spallation is a particular concern for turbine rotor blades and components within combustor, such as liners and transition piece. Early detection of coating spallation may allow an operator to take corrective action before the component becomes completely damaged from the increased thermal strain or the turbine is forced to shut down.

While the operators of combustion turbine engines want to avoid using worn-out or compromised components that risk failing during operation, they also have a competing interests of not prematurely replacing components before their useful life is exhausted. That is, operators want to exhaust the useful life of each component, thereby minimizing part costs while also reducing the frequency of engine outages for part replacements to occur. Accordingly, accurate crack detection and/or coating spallation in engine components is a significant industry need. However, conventional methods generally require regular visual inspection of parts. While useful, visual inspection is both time-consuming and requires the engine be shutdown for a prolonged period.

The ability to monitor components in the hot-gas path while the engine operates for the formation of cracks and the spallation of protective coatings remains a longstanding need. What is needed is a system by which crack formation and spallation may be monitored while the engine operates so that necessary action may be taken before a failure event occurs or significant component damage is realized. Such a system also may extend the life of components as the need for part replacement may be based on actual, measured wear instead of what is anticipated. In addition, such a system would decrease the need or frequency of performing evaluations, such as visual inspections, that require engine shutdown. To the extent that these objectives may be achieved in a cost-effective manner, efficiency would be enhanced and industry demand would be high.

BRIEF DESCRIPTION OF THE INVENTION

The present invention, thus, describes a system for detecting defects in a combustion duct of a combustion system of a combustion turbine engine while the combustion turbine engine operates, wherein the combustion duct comprises a hot side, which is exposed to combustion gases and, opposing the hot side, a cold side. The system may include: an indicator coating disposed on an outer surface of the combustion duct, the indicator coating comprising a detectable substance; and a gas sensor positioned downstream of the combustor, the gas sensor configured to take a measurement of the amount of the detectable substance in the combustion products of the combustion turbine engine.

The present invention further includes a method for detecting defects in a combustion duct of a combustion system of a combustion turbine engine while the combustion turbine engine operates, wherein the combustion duct comprises a hot side, which is exposed to combustion gases and, opposing the hot side, a cold side. The method may include the steps of: coating a cold side the transition piece with an indicator coating, the indicator coating comprising a detectable substance; positioning a gas sensor positioned downstream of the combustor, the gas sensor configured to take a measurement of the amount of the detectable substance in the combustion products of the combustion turbine engine; and using the gas sensor to determine an amount of the detectable substance in the combustion products of the combustion turbine engine.

These and other features of the present application will become apparent upon review of the following detailed description of the preferred embodiments when taken in conjunction with the drawings and the appended claims.

BRIEF DESCRIPTION OF THE DRAWINGS

These and other features of this invention will be more completely understood and appreciated by careful study of the following more detailed description of exemplary embodiments of the invention taken in conjunction with the accompanying drawings, in which.

DETAILED DESCRIPTION OF THE INVENTION

Figure 1:
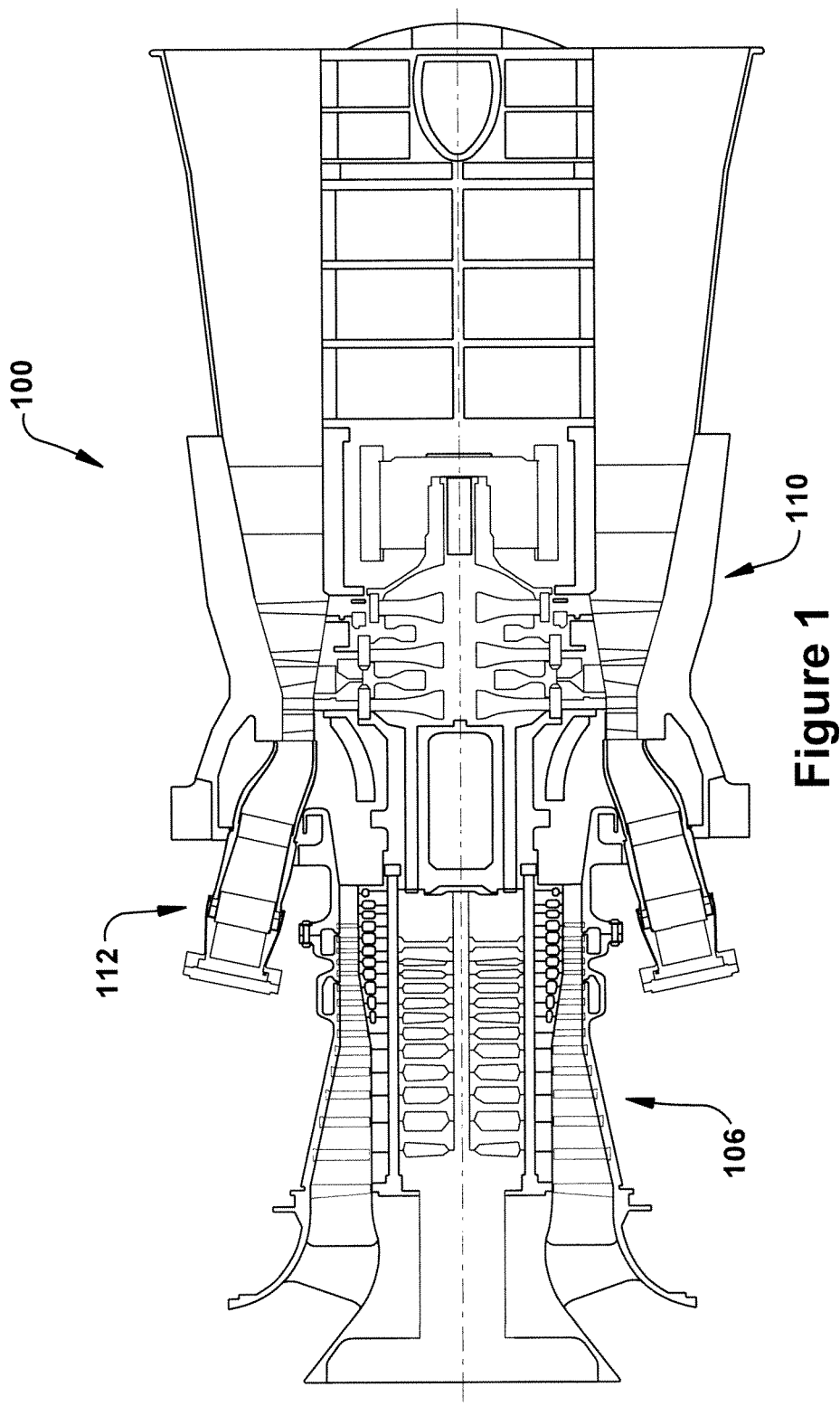
FIG. 1 is a schematic representation of an exemplary turbine engine in which embodiments of the present application may be used.

Referring now to the figures, FIG. 1 illustrates a schematic representation of a gas turbine engine 100 in which embodiments of the present invention may be employed. In general, gas turbine engines operate by extracting energy from a pressurized flow of hot gas that is produced by the combustion of a fuel in a stream of compressed air. As illustrated in FIG. 1, gas turbine engine 100 may be configured with an axial compressor 106 that is mechanically coupled by a common shaft or rotor to a downstream turbine section or turbine 110, and a combustion system 112, which, as shown, is a can combustor that is positioned between the compressor 106 and the turbine 110.

Figure 2:
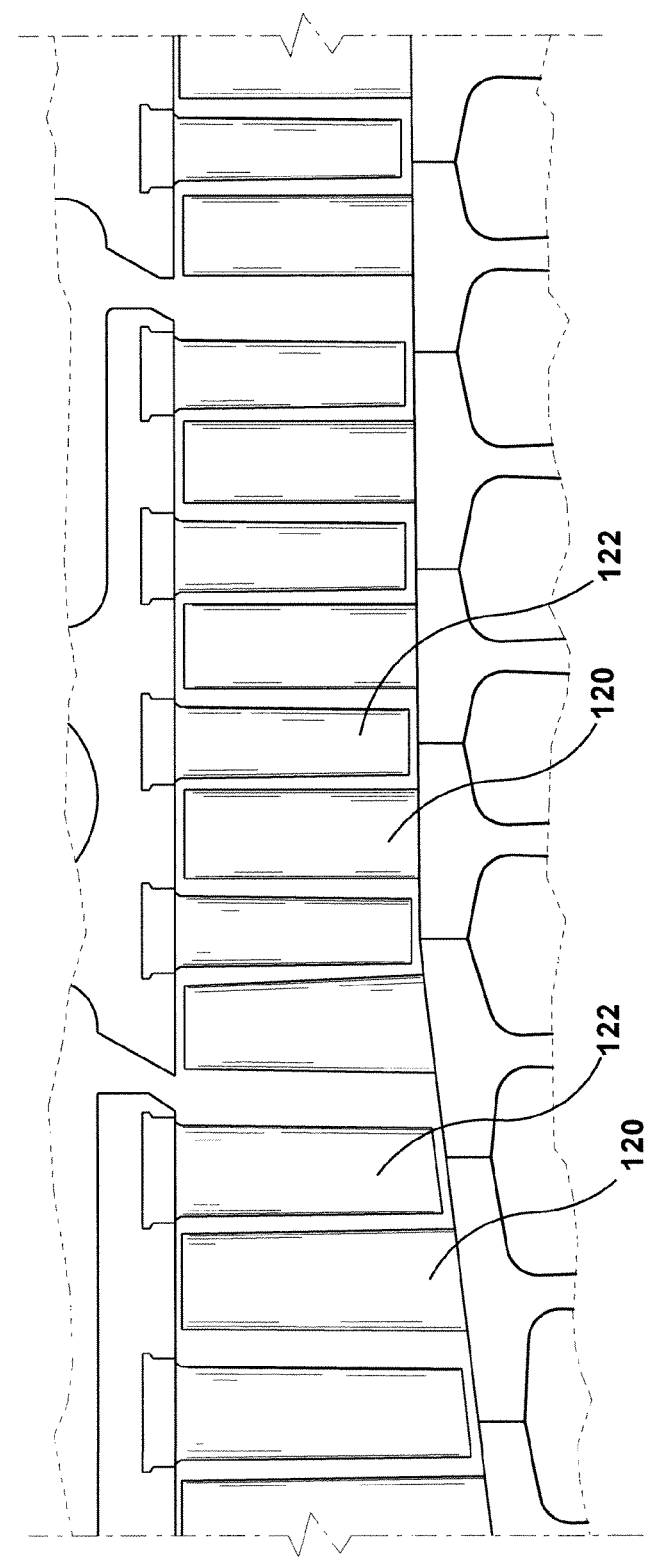
FIG. 2 is a sectional view of an exemplary compressor that may be used in the gas turbine engine of FIG. 1.

FIG. 2 illustrates a view of an axial compressor 106 that may be used in gas turbine engine 100. As shown, the compressor 106 may include a plurality of stages. Each stage may include a row of compressor rotor blades 120 followed by a row of compressor stator blades 122. Thus, a first stage may include a row of compressor rotor blades 120, which rotate about a central shaft, followed by a row of compressor stator blades 122, which remain stationary during operation. The compressor stator blades 122 generally are circumferentially spaced one from the other and fixed about the axis of rotation.

The compressor rotor blades 120 are circumferentially spaced about the axis of the rotor and rotate about the shaft during operation. As one of ordinary skill in the art will appreciate, the compressor rotor blades 120 are configured such that, when spun about the shaft, they impart kinetic energy to the air or working fluid flowing through the compressor 106. As one of ordinary skill in the art will appreciate, the compressor 106 may have many other stages beyond the stages that are illustrated in FIG. 2. Each additional stage may include a plurality of circumferential spaced compressor rotor blades 120 followed by a plurality of circumferentially spaced compressor stator blades 122.

Figure 3:
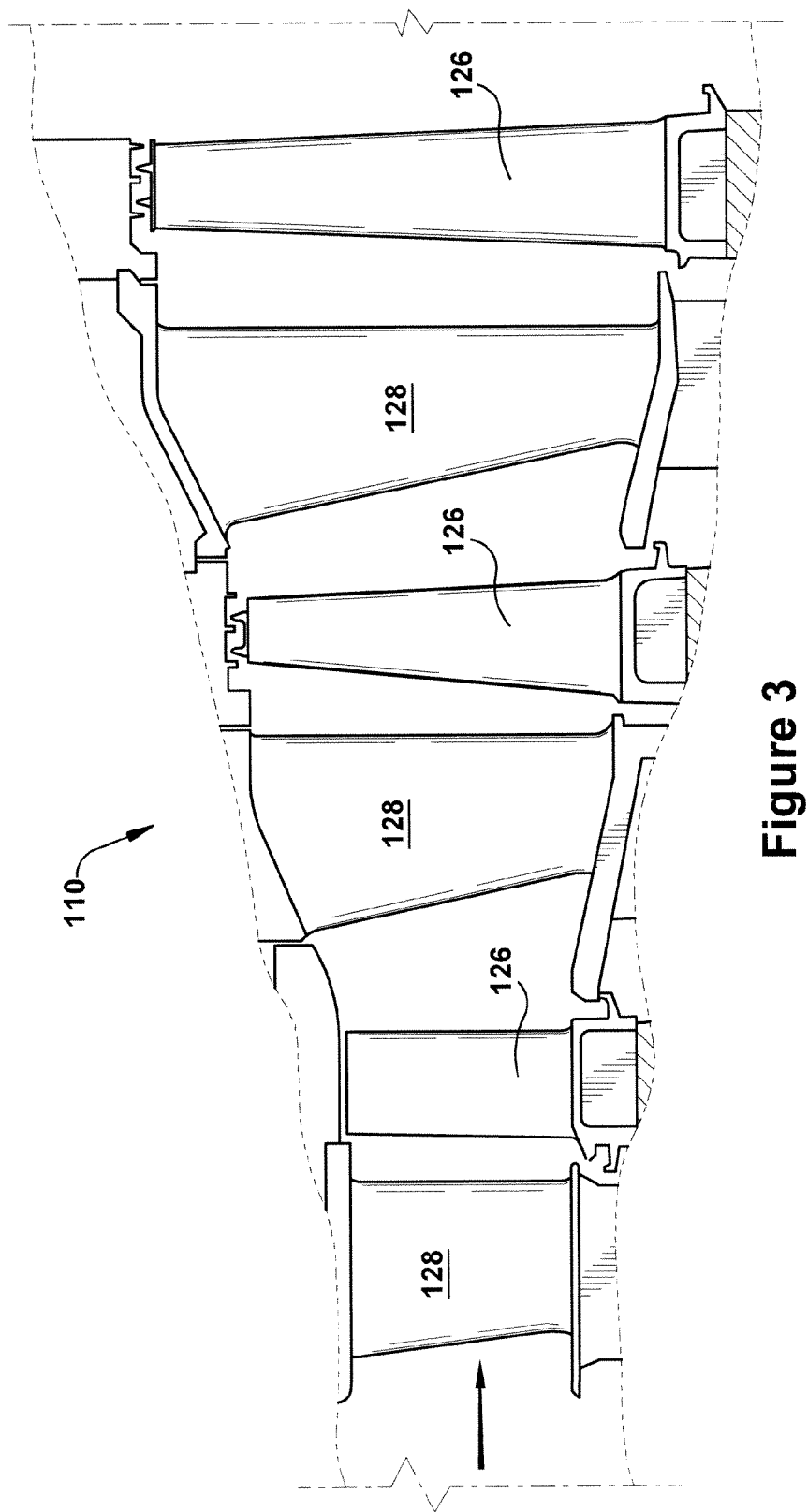
FIG. 3 is a sectional view of an exemplary turbine that may be used in the gas turbine engine of FIG. 1.

FIG. 3 illustrates a partial view of an exemplary turbine section or turbine 110 that may be used in a gas turbine engine 100. The turbine 110 may include a plurality of stages. Three exemplary stages are illustrated, but more or less stages may be present in the turbine 110. A first stage includes a plurality of turbine buckets or turbine rotor blades 126, which rotate about the shaft during operation, and a plurality of nozzles or turbine stator blades 128, which remain stationary during operation. The turbine stator blades 128 generally are circumferentially spaced one from the other and fixed about the axis of rotation. The turbine rotor blades 126 may be mounted on a turbine wheel (not shown) for rotation about the shaft (not shown). A second stage of the turbine 110 is also illustrated. The second stage similarly includes a plurality of circumferentially spaced turbine stator blades 128 followed by a plurality of circumferentially spaced turbine rotor blades 126, which are also mounted on a turbine wheel for rotation. A third stage also is illustrated, and similarly includes a plurality of circumferentially spaced turbine stator blades 128 and turbine rotor blades 126. It will be appreciated that the turbine stator blades 128 and turbine rotor blades 126 lie in the hot gas path of the turbine 110. The direction of flow of the hot gases through the hot gas path is indicated by the arrow. As one of ordinary skill in the art will appreciate, the turbine 110 may have many other stages beyond the stages that are illustrated in FIG. 3. Each additional stage may include a plurality of circumferential spaced turbine stator blades 128 followed by a plurality of circumferentially spaced turbine rotor blades 126.

A gas turbine engine of the nature described above may operate as follows. The rotation of compressor rotor blades 120 within the axial compressor 106 compresses a flow of air. In the combustor 112, as described in more detail below, energy is released when the compressed air is mixed with a fuel and ignited. The resulting flow of hot gases from the combustor 112 then may be directed over the turbine rotor blades 126, which may induce the rotation of the turbine rotor blades 126 about the shaft, thus transforming the energy of the hot flow of gases into the mechanical energy of the rotating shaft. The mechanical energy of the shaft may then be used to drive the rotation of the compressor rotor blades 120, such that the necessary supply of compressed air is produced, and also, for example, a generator to produce electricity.

Before proceeding further, it will be appreciated that in order to communicate clearly the present invention, it will become necessary to select terminology that refers to and describes certain parts or machine components of a turbine engine and related systems, particularly, the combustor system. Whenever possible, industry terminology will be used and employed in a manner consistent with its accepted meaning. However, it is meant that any such terminology be given a broad meaning and not narrowly construed such that the meaning intended herein and the scope of the appended claims is unreasonably restricted. Those of ordinary skill in the art will appreciate that often a particular component may be referred to using several different terms. In addition, what may be described herein as a single part may include and be referenced in another context as consisting of several component parts, or, what may be described herein as including multiple component parts may be fashioned into and, in some cases, referred to as a single part. As such, in understanding the scope of the invention described herein, attention should not only be paid to the terminology and description provided, but also to the structure, configuration, function, and/or usage of the component, as provided herein.

In addition, several descriptive terms may be used regularly herein, and it may be helpful to define these terms at this point. These terms and their definition given their usage herein is as follows. The term "rotor blade", without further specificity, is a reference to the rotating blades of either the compressor or the turbine, which include both compressor rotor blades and turbine rotor blades. The term "stator blade", without further specificity, is a reference the stationary blades of either the compressor or the turbine, which include both compressor stator blades and turbine stator blades. The term "blades" will be used herein to refer to either type of blade. Thus, without further specificity, the term "blades" is inclusive to all type of turbine engine blades, including compressor rotor blades, compressor stator blades, turbine rotor blades, and turbine stator blades. Further, as used herein, "downstream" and "upstream" are terms that indicate a direction relative to the flow of a fluid, such as the working fluid through the turbine. As such, the term "downstream" refers to a direction that generally corresponds to the direction of the flow of working fluid, and the term "upstream" generally refers to the direction that is opposite of the direction of flow of working fluid. The terms "forward" or "leading" and "aft" or "trailing" generally refer to relative position in relation to the forward end and aft end of the turbine engine (i.e., the compressor is the forward end of the engine and the end having the turbine is the aft end). At times, which will be clear given the description, the terms "leading" and "trailing" may refer to the direction of rotation for rotating parts. When this is the case, the "leading edge" of a rotating part is the edge that leads in the rotation and the "trailing edge" is the edge that trails.

The term "radial" refers to movement or position perpendicular to an axis. It is often required to described parts that are at differing radial positions with regard to an axis. In this case, if a first component resides closer to the axis than a second component, it may be stated herein that the first component is "radially inward" or "inboard" of the second component. If, on the other hand, the first component resides further from the axis than the second component, it may be stated herein that the first component is "radially outward" or "outboard" of the second component. The term "axial" refers to movement or position parallel to an axis. Finally, the terms "circumferential" or "angular position" refers to movement or position around an axis.

Figure 4:
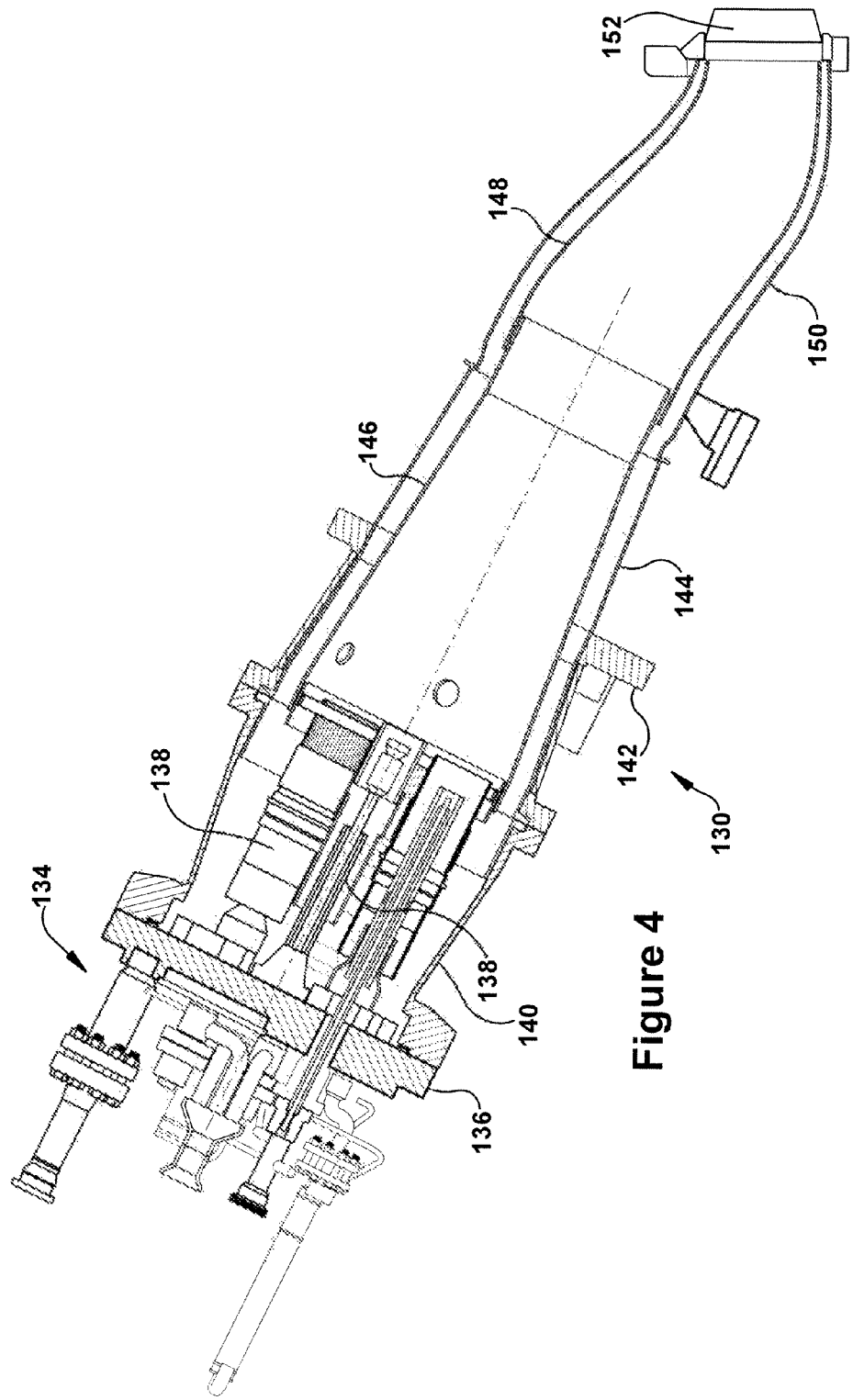
FIG. 4 is a sectional view of an exemplary combustor that may be used in the gas turbine engine of FIG. 1 and in which the present invention may be employed.
Figure 5:
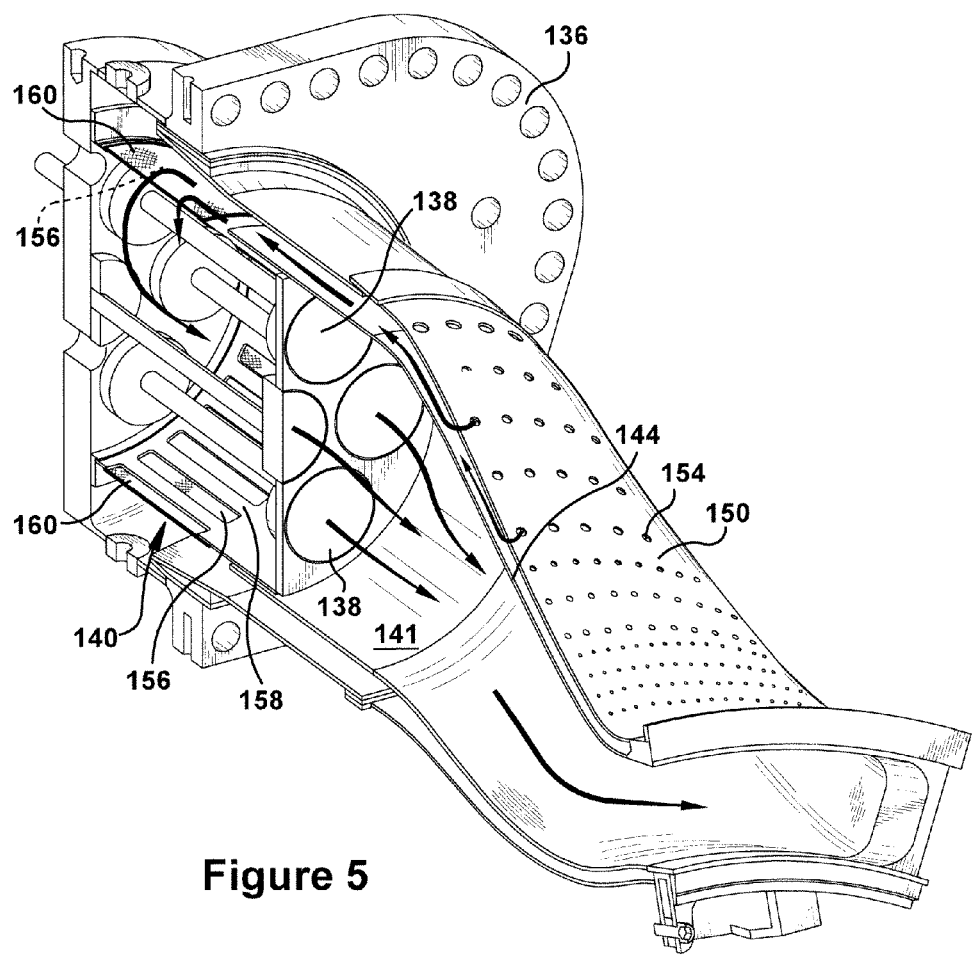
FIG. 5 is a perspective cutaway of an exemplary combustor in which embodiments of the present invention may be employed.

FIGS. 4 and 5 illustrates an exemplary combustor 130 that may be used in a gas turbine engine and in which embodiments of the present invention may be used. As one of ordinary skill in the art will appreciate, the combustor 130 may include a headend 163, which generally includes the various manifolds that supply the necessary air and fuel to the combustor, and an end cover 170. A plurality of fuel lines 137 may extend through the end cover 170 to fuel nozzles or fuel injectors 138 that are positioned at the aft end of a forward case or cap assembly 140. It will be appreciated that the cap assembly 140 generally is cylindrical in shape and fixed at a forward end to the end cover 170.

In general, the fuel injectors 138 bring together a mixture of fuel and air for combustion. The fuel, for example, may be natural gas and the air may be compressed air (the flow of which is indicated in FIG. 4 by the several arrows) supplied from the compressor. As one of ordinary skill in the art will appreciate, downstream of the fuel injectors 138 is a combustion chamber 180 in which the combustion occurs. The combustion chamber 180 is generally defined by a liner 146, which is enclosed within a flow sleeve 144. Between the flow sleeve 144 and the liner 146 an annulus is formed. From the liner 146, a transition piece 148 transitions the flow from the circular cross section of the liner to an annular cross section as it travels downstream to the turbine section (not shown in FIG. 4). A transition piece impingement sleeve 150 (hereinafter "impingement sleeve 150") may enclose the transition piece 148, also creating an annulus between the impingement sleeve 150 and the transition piece 148. At the downstream end of the transition piece 148, a transition piece aft frame 152 may direct the flow of the working fluid toward the airfoils that are positioned in the first stage of the turbine 110. It will be appreciated that the flow sleeve 144 and the impingement sleeve 150 typically has impingement apertures (not shown in FIG. 4) formed therethrough which allow an impinged flow of compressed air from the compressor 106 to enter the cavities formed between the flow sleeve 144 and the liner 146 and between the impingement sleeve 150 and the transition piece 148. The flow of compressed air through the impingement apertures convectively cools the exterior surfaces of the liner 146 and the transition piece 148.

Referring now to FIGS. 6 through 12, several methods for detecting defects within the transition piece 148 within a combustion turbine engine will be discussed. It will be appreciated that reference to "defects" includes both the formation of cracks within the transition piece 148 and the spallation of the protective coating (i.e., thermal barrier coating) that is typically applied to the interior surface of the transition piece.

Figure 6:
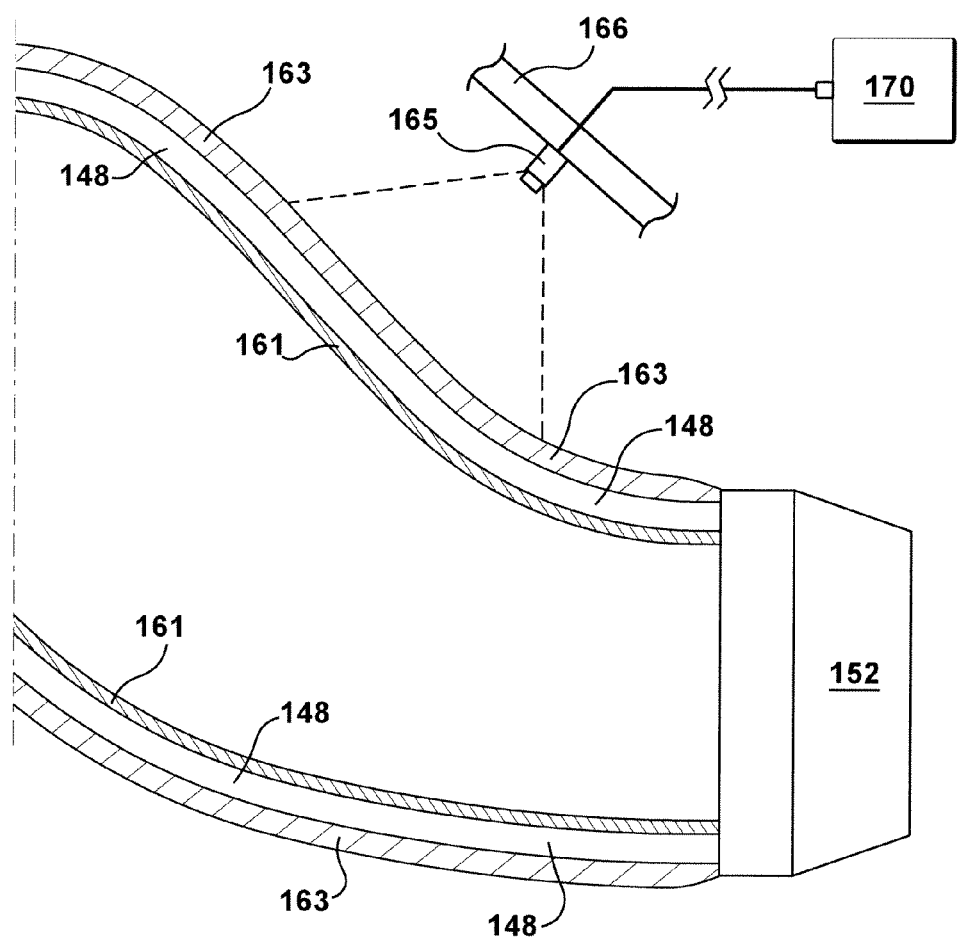
FIG. 6 illustrates a cross-sectional view of a transition piece and a system for monitoring material defects according to an exemplary embodiment of the present invention.
Figure 7:
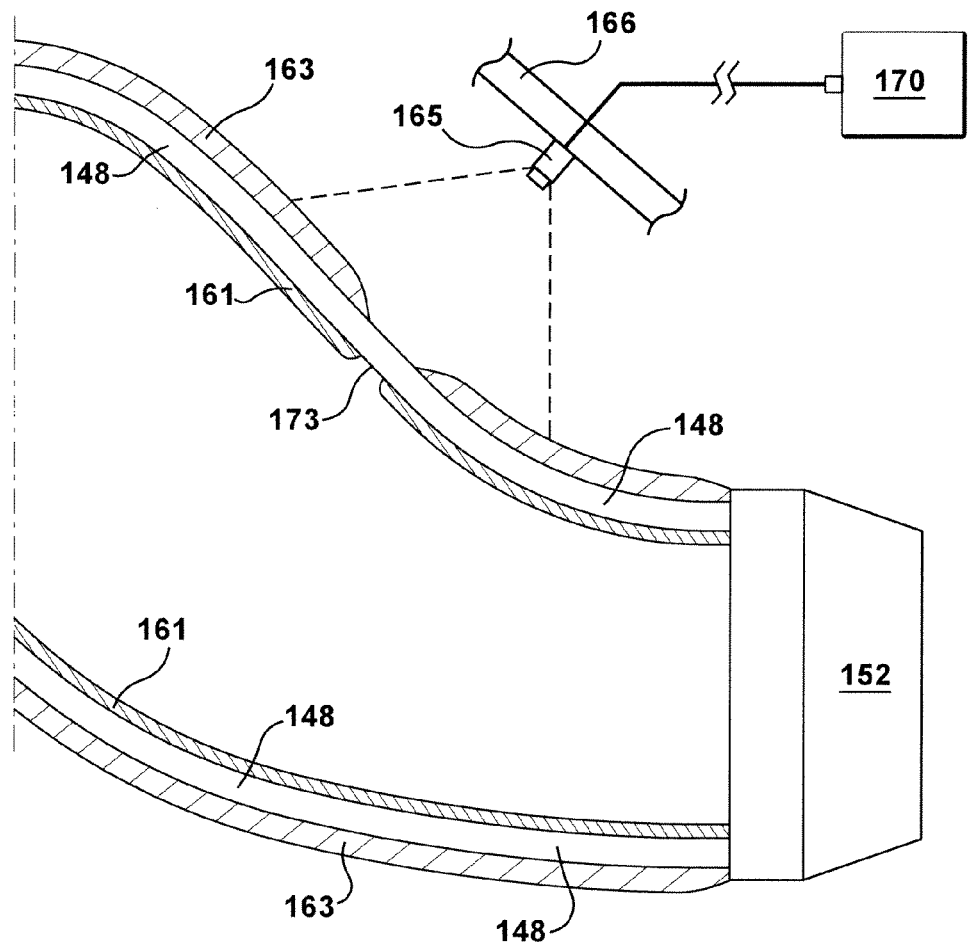
FIG. 7 illustrates the system of FIG. 6 as it may detect a defect according to an embodiment of the present invention.

FIG. 6 illustrates a cross-sectional view of a transition piece 148 and a system for monitoring material defects within the transition piece 148 according to an embodiment of the present invention. (It will be appreciated by those of ordinary skill in the art that the systems and methods described herein may be applied in the same manner to liners 146 within the combustion system. The usage of the transition piece 148 in the several exemplary uses are provided below, accordingly, is meant to apply also to users within the liner 146 of the combustor. When referred to jointly in the appended claims, the transition piece 148 and liner 146 will be referred to as a "combustion duct") FIG. 7 illustrates the operation of the system as it detects a defect within the transition piece 148 according to an exemplary embodiment. It will be appreciated that the interior surface of the transition piece 148, which is often referred to as the "hot side", may be coated with a protective coating 161, which may be a conventional thermal barrier coating. According to the present invention, the exterior surface of the transition piece 148, which is often referred to as the "cold side", may be coated with an indicator coating 163. In one embodiment, the indicator coating 163, as described in more detail below, may include coating that includes a powder substance, such as zinc, cadmium, magnesium, or any other colorful powder, and an adhesive. In some embodiments the adhesive may include ceramic adhesives (Resbond™ 919 & 920), ceramic putties, or epoxy silicones, which have good creep resistance properties at high temperatures, or other similar types of materials or adhesives. As shown, the indicator coating 163 may be applied to large areas of the cold side of the transition piece 148. It will be appreciated that the adhesive will bind the coating to the cold side of transition piece 148.

According to embodiments of the present invention, a detector 165 may be positioned such that it detects light that is either reflected or emanating from the cold side of the transition piece 148, as illustrated in FIG. 6. The detector 165 may be connected to stationary structure 166 such that its position and ability to monitor the cold side of the transition piece 148 remains stable. The detector 165 may be position such that a particular area of the transition piece 148 is within the detector's 148 field of view. In some embodiments, the stationary structure 166 may include a section of the combustor casing. In other embodiments, the stationary structure 166 may include a section of the impingement sleeve 150 that surrounds the transition piece 148. The detector 165 may be positioned a predetermined distance from transition piece 148 such that a desirable coverage area is achieved.

In one embodiment, the detector 165 comprises a conventional photosensor or photodetector, i.e., a conventional sensor that is able to detect light. More specifically, the detector may comprises any conventional photodetector that is capable of detecting the changes to the indicator coating 163 that are described herein. According to one embodiment, the detector 165 comprises a conventional color sensor, which may include a Bayer type sensor, a Foveon X3 type sensor, a 3CCD type sensor or other type of color sensor. According to an alternative embodiment, the detector 165 comprises a photodiode light sensor or other type of photodetector configured to detect bright light or light flashes that may occur upon the combustion of substances that may be used to dope the indicator coating 163.

As illustrated in FIG. 6, the detector 165 may be in communication with a control unit 170 that is configured to determine whether color or light has been detected by the detector 165 that exceeds predetermined criteria. In the event that the predetermined criteria has been crossed, the control unit 170 may then be configured to send an automatic warning signal or perform a corrective action. For example, the warning signal may comprise an alarm or other communication, such as an e-mail or automated message, to an operator, and the corrective action may include shutting down the combustion turbine engine.

In operation, the adhesive of the indicator coating 163 binds the powder of the coating to the cold side of the transition piece 148. Absent the formation of a defect 173, it will be appreciated that the indicator coating 163 may be configured such that it remains bound to the cold side of the transition piece 148 and, accordingly, the detector 165 registers no change in the light reflected or admitted therefrom.

As illustrated in FIG. 7, a defect 173 may form within the transition piece 148. As stated, the defect 173 may include a crack within the transition piece 148 that causes the spallation of protective coating 161, or the defect 173 may include erosion or spallation of protective coating 161 from the transition piece 148. With the formation of the defect 173, the temperature of the transition piece 148 will increase and result in a "hotspot" forming along a section of the cold side of the transition piece 148. In the case of a defect 173 that includes a crack through the transition piece 148, this may include hot gases being ingested through the crack, which may cause an even greater increase in temperature along the cold side of the transition piece 148.

Given the increase in temperature, according to an embodiment of the present invention, it will be appreciated that the coating may be configured such that the adhesive begins to lose its adhesive characteristics and/or the powder substance begins melting. As one of ordinary skill in the art will appreciate, these conditions may cause the cold side of the transition piece 148 to lose its coverage of the indicator coating 163, i.e., develop bare patches as illustrated in FIG. 7. In the case where the detector 165 comprises a color sensor, this will cause a change in color that may be detected by the detector 165. For example, the color of the cold side of the transition piece 148 may change due to thermal distress. Or, for example, the color of the cold side of the transition piece 148 may be gray, while the indicator coating was white, such that the removal of the indicator coating 163 causes a distinct color change. As stated, in exemplary embodiments, the detection of the change in color may cause the control unit 170 to provide a warning notification that a defect 173 is likely and/or that corrective action should be taken. It will be appreciated that the sensitivity of the system may be adjusted by using different criteria concerning the signal received from the detector before a warning notification is issued.

In an alternative embodiment, the indicator coating 163 may include a material, such as magnesium, that admits bright light and/or bright flashes upon being subject to the high temperatures of ingested hot path gases. In another manner, this event could also be detected, after the coating spalls (due to material melting or loss of adhesion property) and flows along the cold side of the transition piece 148 to the air inlet (not shown) of the combustor or through the leakage path between transition piece and liner (hula seal path) or through a crack. The loose pieces 163*a* may combust and thereby release the detectable bright light at the hot side of transition piece/liner which could be detected by a spectroscope installed either at transition piece aft end or at stack (similarly to the system illustrated in FIGS. 10 through 12). In this case, the detector 165 may include a photodetector or spectroscope that is capable of registering such bright light and/or bright flashes. For example, the detector 165 may include a photodiode. In this case, the raised temperatures and/or ingested gases that may occur upon the formation of a defect 173 may cause the magnesium or other such material to produce the bright light or bright flashes. In exemplary embodiments, the detection of the bright light/flashes may cause the control unit 170 to provide a warning notification that a defect 173 is likely and/or that corrective action should be taken. It will be appreciated that the sensitivity of the system may be adjusted by using different criteria concerning the signal received from the detector 165 before a warning notification is issued.

In another alternative embodiment, the two prior embodiments may form a combined embodiment that detects both color change and bright lights/flashes. It will be appreciated that in such an embodiment the different modes of detection may be configured to communicate varying categories of defects 173. For example, the detection of a color change by the detector 165 may indicate a hotspot resulting from the erosion of protective coating 161 from the inner surface of the transition piece 148. The detection of the bright light/flashes, on the other hand, may indicate a more serious problem that includes the ingestion of hot flow path gases through a crack in the transition piece 148. In any case, the parameters, of course, may be adjusted depending on the characteristics of the system and the desired sensitivity, as one of ordinary skill in the art will appreciate.

Figure 8:
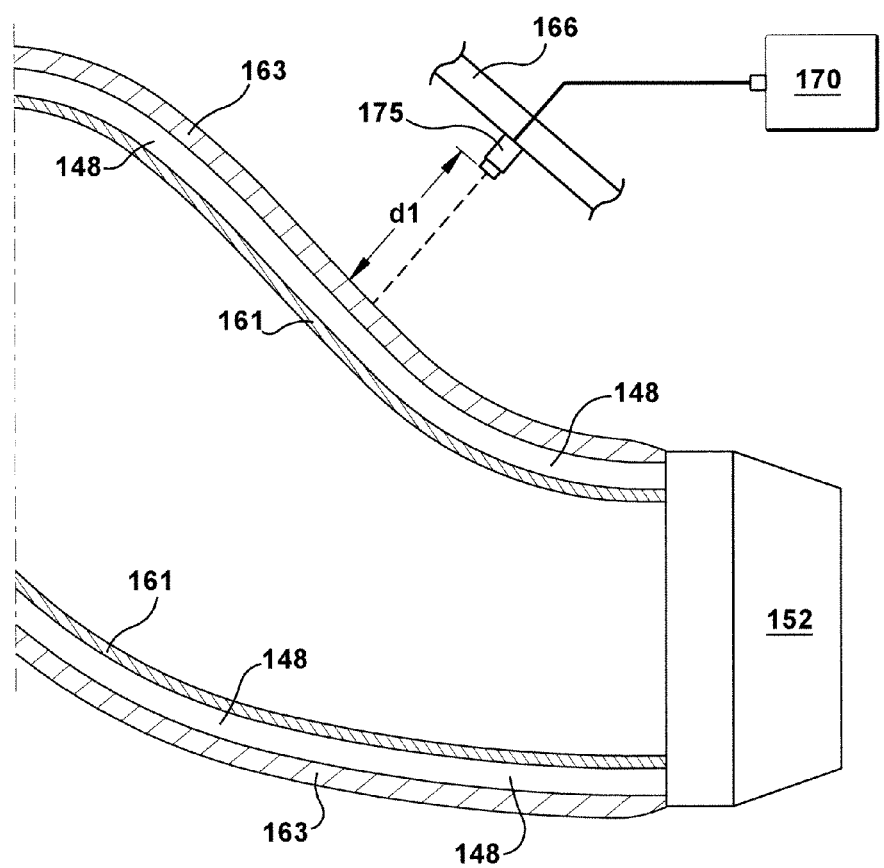
FIG. 8 illustrates cross-sectional view of a transition piece and a system for monitoring material defects according to an alternative embodiment of the present invention.
Figure 9:
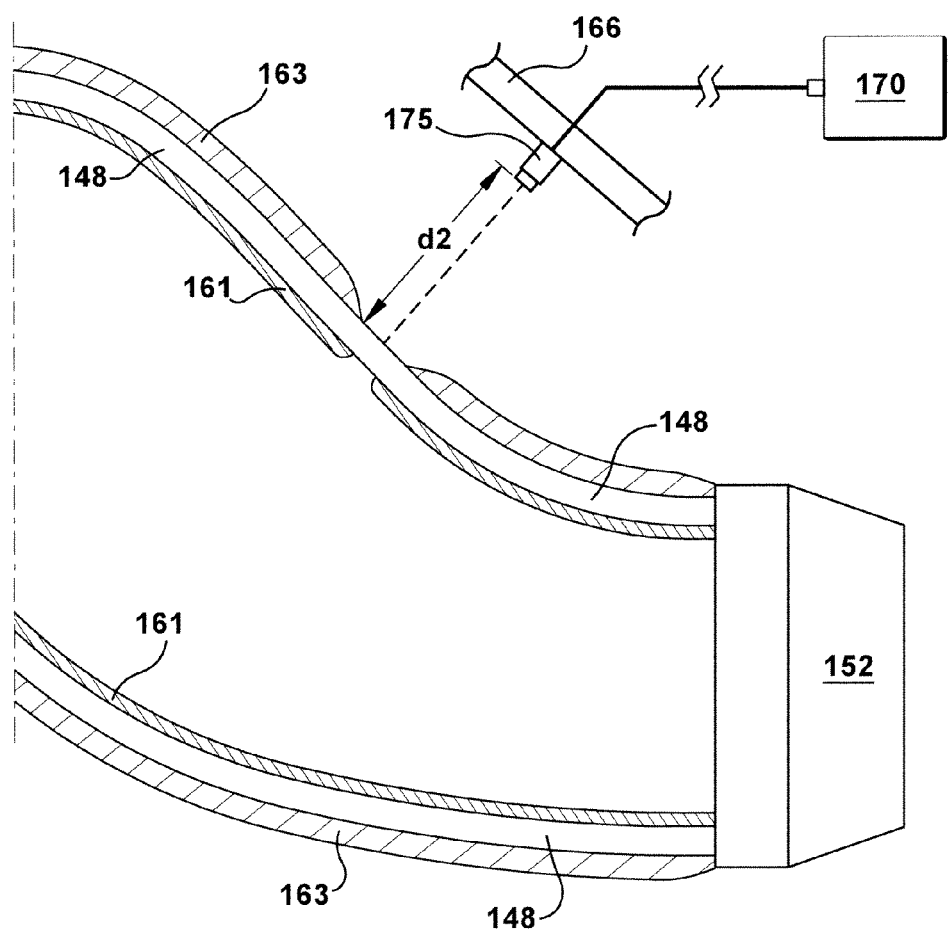
FIG. 9 illustrates the system of FIG. 8 as it may detect a defect according to an embodiment of the present invention.

FIG. 8 illustrates a cross-sectional view of a transition piece and a system for monitoring material defects according to the present invention, while FIG. 9 illustrates the operation of the system as it detects a defect according to an exemplary embodiment.

Similar to the embodiments discussed above, the interior surface of the transition piece may be coated with a protective coating 161, which may be a conventional thermal barrier coating. The exterior surface of the transition piece 148, may be coated with an indicator coating 163. In this embodiment, the indicator coating 163 may be any conventional coating that fulfills the performance criteria described herein. For example, the indicator coating 163, in some preferred embodiments, may include ceramic adhesives, ceramic putties, or epoxy silicones, which have good creep resistance properties at high temperatures, or other similar types of materials or adhesives. As shown, the indicator coating 163 may be applied to large areas of the cold side of the transition piece 148. It will be appreciated that the adhesive qualities of the coating will bind the indicator coating to the cold side of transition piece 148. In preferred embodiments, the indicator coating 161 may be applied such that it has a thickness of approximately 0.001 to 0.80 inches.

According to alternative embodiments of the present invention, a proximity sensor 175 may be connected to stationary structure 166 such that its position in relation to the transition piece 148 is fixed. The proximity sensor 175 may be position such that a particular area of the transition piece 148 is within the field of view of the proximity sensor 175. In some embodiments, the stationary structure 166 may include a section of the combustor casing. In other embodiments, the stationary structure 166 may include a section of the impingement sleeve 150 that surrounds the transition piece 148. The detector 165 may be positioned a suitable distance from transition piece 148 according to the performance characteristics of the particular proximity sensor 175. In one preferred embodiment, the proximity sensor 120 is a laser proximity probe. In other embodiments, the proximity sensor 120 may be an eddy current sensor, capacitive sensor, microwave sensor, or any other similar type of device.

As illustrated in FIG. 8, the proximity sensor 175 may be in communication with a control unit 170 that is configured to determine whether a change in the distance between the proximity sensor and the indicator coating 163 has been detected by the proximity sensor 175 that exceeds predetermined criteria. In the event that the predetermined criteria has been exceeded, the control unit 170 may then be configured to send an automatic warning signal or perform a corrective action. For example, the warning signal may comprise an alarm or other communication, such as an e-mail or automated message, to an operator, and the corrective action may include shutting down the combustion turbine engine.

In operation, the adhesive of the indicator coating 163 generally binds the coating to the cold side of the transition piece 148. Absent the formation of a defect 173, it will be appreciated that the indicator coating 163 may be configured such that it remains bound to the cold side of the transition piece 148 and, accordingly, the proximity sensor 175 registers no change in the distance (which is indicated as "d1" in FIG. 8) to the surface of the indicator coating 163.

As illustrated in FIG. 9, a defect 173 may form within the transition piece 148. As stated, the defect 173 may include a crack within the transition piece 148 that causes the spallation of protective coating 161, or the defect 173 may include erosion or spallation of protective coating 161 from the transition piece 148 that forms in the absence of a crack within the transition piece 148. With the formation of the defect 173, the temperature of the transition piece 148 will increase and result in a "hotspot" forming along a section of the cold side of the transition piece 148. In the case of a defect 173 that includes a crack through the transition piece 148, this may include hot gases being ingested through the crack, which may cause an even greater increase in temperature along the cold side of the transition piece 148.

Given the increase in temperature, according to an embodiment of the present invention, it will be appreciated that the coating may be configured such that the adhesive begins to lose its adhesive characteristics and/or the powder substance begins melting. As one of ordinary skill in the art will appreciate, these conditions may cause the cold side of the transition piece 148 to lose its coverage of the indicator coating 163, i.e., develop bare patches as illustrated in FIG. 7. The proximity sensor 175 may measure a change in the distance to the transition piece 148 (i.e., the proximity sensor 175 may indicate the distance has increased to the distance indicated as "d2" in FIG. 9). In exemplary embodiments, the detection of the change in distance may cause the control unit 170 to provide a warning notification that a defect 173 is likely and/or that corrective action should be taken. It will be appreciated that the sensitivity of the system may be adjusted by using different criteria concerning the change in distance required before a warning notification is issued.

Figure 10:
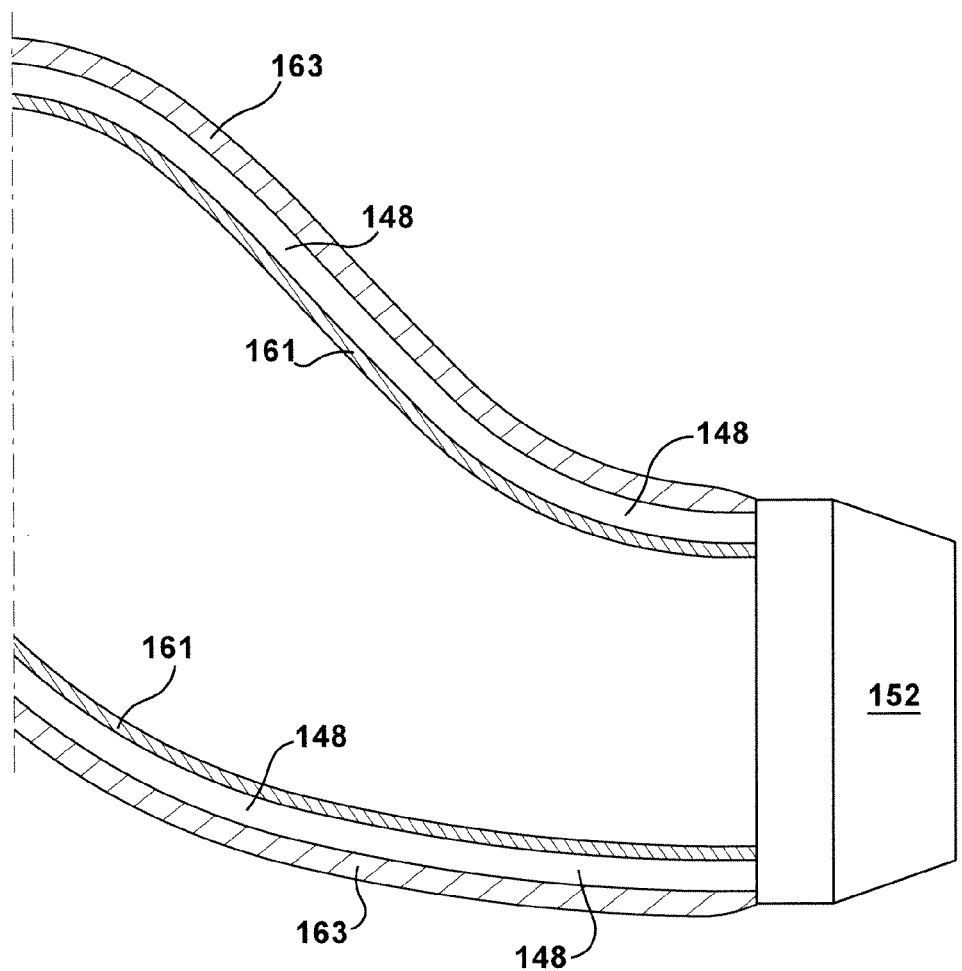
FIG. 10 illustrates cross-sectional view of a transition piece and a system for monitoring material defects according to an alternative embodiment of the present invention.
Figure 11:
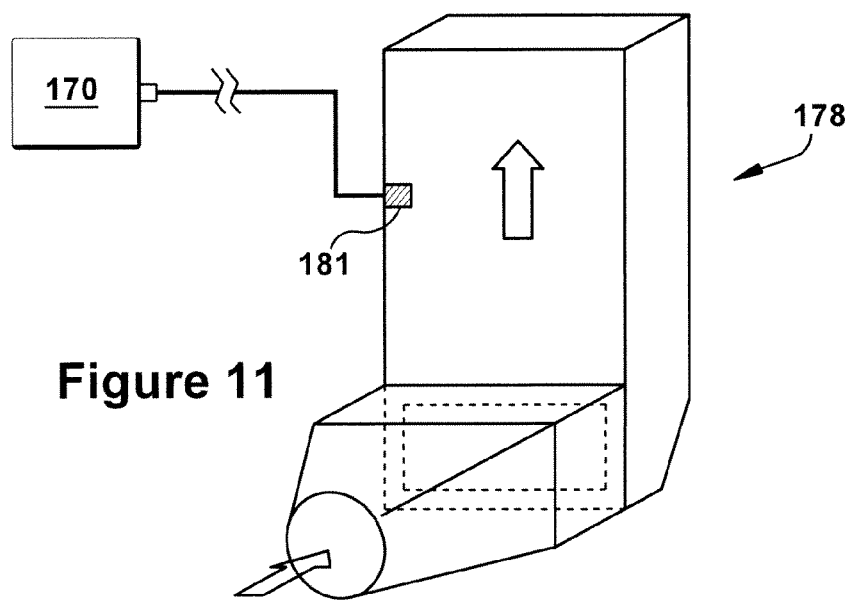
FIG. 11 illustrates a schematic representation of a stack for a combustion turbine engine and a detector according to the embodiment of FIG. 10.
Figure 12:
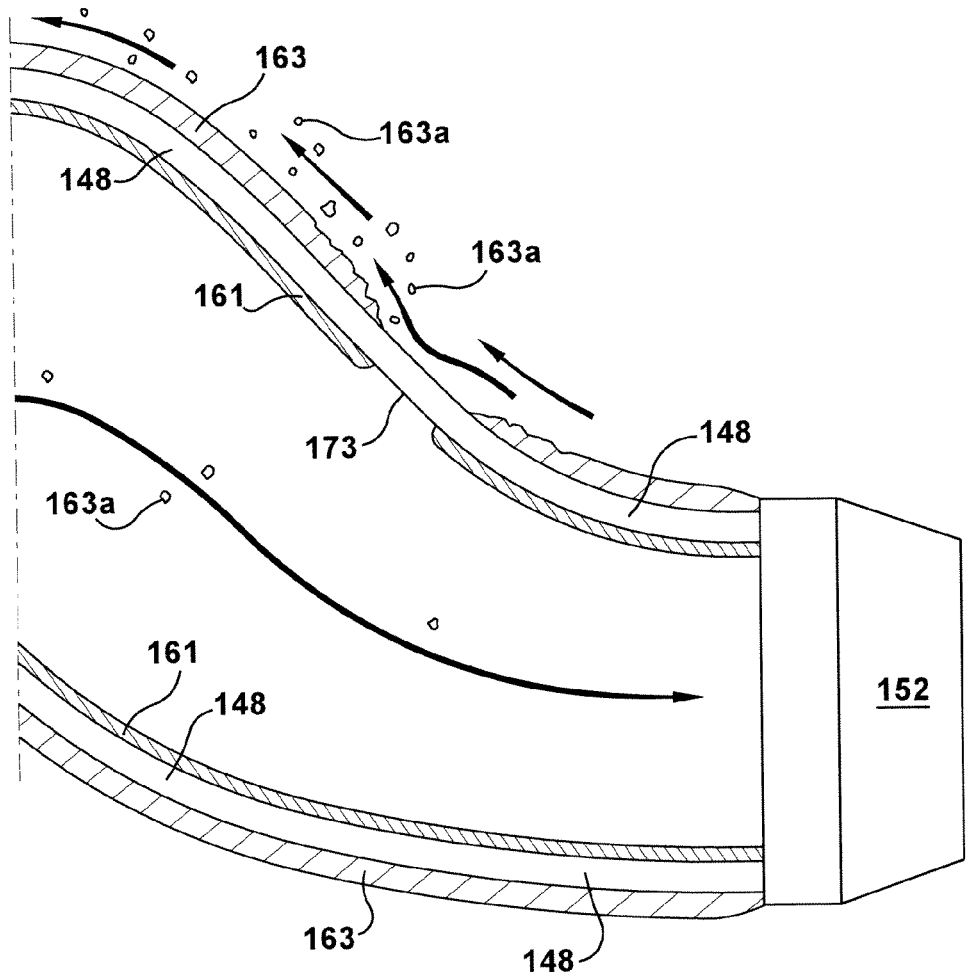
FIG. 12 illustrates the system of FIGS. 10 and 11 as it may detect a defect according to an embodiment of the present invention.

FIGS. 10 and 11 illustrate a view of a transition piece and downstream stack, respectively, that include a system for monitoring material defects according to the present invention, while FIG. 12 illustrates the operation of the system as it detects a defect according to an exemplary embodiment.

Similar to the embodiments discussed above, the interior surface of the transition piece may be coated with a protective coating 161, which may be a conventional thermal barrier coating. The exterior surface of the transition piece 148, may be coated with an indicator coating 163. In this embodiment, the indicator coating 163, as described in more detail below, may be ceramic adhesives, ceramic putties, or epoxy silicones, which have good creep resistance properties at high temperatures, or other similar types of materials or adhesives. As described in more detail below, the indicator coating 163 may include a substance which is detectable by a gas analyzer or sensor 181 located downstream. In certain preferred embodiments, this detectable substance is a rare earth element. In other embodiments, the detectable substance may be cadmium or magnesium. It will be appreciated that other substances may also be used. As shown, the indicator coating 163 may be applied to large areas of the cold side of the transition piece 148. It will be appreciated that the adhesive qualities of the coating will bind the indicator coating to the cold side of transition piece 148.

According to alternative embodiments of the present invention, as stated, a gas analyzer 181 may be located in a suitable location downstream of the combustor. Once such preferred locations is within the stack 178 of the combustion turbine engine, as illustrated in FIG. 11. The gas sensor 181 may include any conventional gas analyzer suitable for the described application, as one of ordinary skill may or will appreciate. In a preferred embodiment, the gas sensor 181 comprises a chromatography analyzer. Other types of conventional gas sensors may also be used.

As illustrated in FIG. 11, the gas sensor 181 may be in communication with a control unit 170 that is configured to determine whether the gas being analyzed includes the detectable substance of the indicator coating 163. The control unit 170 may be configured to determine whether a predetermined threshold of the detectable substance has been exceeded. In the event that the predetermined threshold has been exceeded, the control unit 170 may then be configured to send an automatic warning signal or perform a corrective action. For example, the warning signal may comprise an alarm or other communication, such as an e-mail or automated message, to an operator, and the corrective action may include shutting down the combustion turbine engine.

In operation, the adhesive of the indicator coating 163 generally binds the coating to the cold side of the transition piece 148. Absent the formation of a defect 173, it will be appreciated that the indicator coating 163 may be configured such that it remains bound to the cold side of the transition piece 148 and, accordingly, the gas sensor registers no detection of the detectable substance of indicator coating 161 within the combustion products flowing through the stack 170.

As illustrated in FIG. 9, a defect 173 may form within the transition piece 148. As stated, the defect 173 may include a crack within the transition piece 148 that causes the spallation of protective coating 161, or the defect 173 may include erosion or spallation of protective coating 161 from the transition piece 148 that forms in the absence of a crack within the transition piece 148. With the formation of the defect 173, the temperature of the transition piece 148 will increase and result in a "hotspot" forming along a section of the cold side of the transition piece 148. In the case of a defect 173 that includes a crack through the transition piece 148, this may include hot gases being ingested through the crack, which may cause an even greater increase in temperature along the cold side of the transition piece 148.

Given the increase in temperature, according to an embodiment of the present invention, it will be appreciated that the coating may be configured such that the adhesive begins to lose its adhesive characteristics and/or the powder substance begins melting. As one of ordinary skill in the art will appreciate, these conditions may cause the indicator coating 163 to erode from cold side of the transition piece 148. Pieces of the eroded indicator coating (which are indicated as "163a" in FIG. 12) may flow along the cold side of the transition piece 148 to the air inlet (not shown) of the combustor. The loose pieces 163a may combust and thereby release the detectable substance within the indicator coating 161. Alternatively, the detectable substance may be released upon the development of a hotspot and/or ingested into the hot gas flow path through a crack formed through the transition piece 148.

The gas sensor 181, which, as stated, is located downstream of the combustor, and, in one preferred embodiment, within the stack 178, then may detect the detectable substance of the indicator coating 163. In exemplary embodiments, the detection of the detectable substance may cause the control unit 170 to provide a warning notification that a defect 173 is likely and/or that corrective action should be taken. It will be appreciated that the sensitivity of the system may be adjusted by requiring different threshold levels of the substance be detected before a corrective action is taken. In this manner, the catastrophic failure of transition piece may be avoided.

Alternatively, according to another embodiment of the present invention, the protective coating 161 (for example, the thermal barrier coating) on hot side of transition piece 148 could be doped with the detectable substance. The gas sensor 181 at the stack 178 or other downstream location then may detect the traces of the detectable substance as the protective coating 161 spalls. This will be indicative of protective coating spallation and/or crack formation.

It will be appreciated that by monitoring crack formation and coating spallation while the engine operates may reduce the need for regular visual inspections, which may also reduce engine down time. As will be appreciated, typically the transition piece is not inspected until the combustion system undergoes a diagnostic check after several thousands of hours of operation. Monitoring for crack formation and spallation while the engine operates may detect the formation of a significant defect that otherwise would have gone unnoticed until this inspection occurs. Depending on the severity of the defect, significant damage may occur if the engine continues to operate and corrective action is not taken, particularly if a failure liberates pieces of the transition piece that cause damage to downstream components. Such an event may be avoided if the real-time monitoring capabilities of the present invention are available.

As one of ordinary skill in the art will appreciate, the many varying features and configurations described above in relation to the several exemplary embodiments may be further selectively applied to form the other possible embodiments of the present invention. For the sake of brevity and taking into account the abilities of one of ordinary skill in the art, all of the possible iterations is not provided or discussed in detail, though all combinations and possible embodiments embraced by the several claims below or otherwise are intended to be part of the instant application. In addition, from the above description of several exemplary embodiments of the invention, those skilled in the art will perceive improvements, changes and modifications. Such improvements, changes and modifications within the skill of the art are also intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

We claim:

1. A system for detecting defects in a combustion duct of a combustion system of a combustion turbine engine while the combustion turbine engine operates, wherein the combustion duct comprises a hot side, which is exposed to combustion gases and, opposing the hot side, a cold side, the system comprising:
   an indicator coating disposed on the cold side of the combustion duct, the indicator coating comprising a detectable substance, the indicator coating degrading above a threshold temperature; and
   a gas sensor positioned downstream of the combustor, the gas sensor configured to take a measurement of the amount of the detectable substance in the combustion products of the combustion turbine engine.

2. The system according to claim 1, wherein the indicator coating is configured such that the degradation above the threshold temperature causes the indicator coating to detach from the cold side of the combustion duct.

3. The system according to claim 2, wherein the hot side comprises a protective coating; and
   wherein the threshold temperature corresponds to an elevated temperature that results from a defect in the protective coating of the hot side.

4. The system according to claim 3, wherein the defect comprises spallation of the protective coating from an area on the hot side, the area of spallation comprising at least a threshold size, wherein the threshold size corresponds to the size required to cause the threshold temperature at the cold side.

5. The system according to claim 3, wherein the combustion duct comprises at least one of a transition piece and a liner; wherein the protective coating comprises a thermal barrier coating; and wherein the indicator coating comprises an adhesive and the adhesive of the indicator coating comprises one of a ceramic adhesive, a ceramic putty, and an epoxy silicone.

6. The system according to claim 2, further comprising a control unit that communicates with the gas sensor;

wherein the control unit and gas sensor are configured to take and record an initial measurement of the amount of the detectable substance in the combustion products of the combustion turbine engine; and wherein the control unit and gas sensor are configured to take and record a subsequent measurement of the amount of the detectable substance in the combustion products of the combustion turbine engine.

7. The system according to claim 6, wherein the control unit is configured to compare the initial measurement against the subsequent measurement to determine if the amount of the detectable substance in the combustion products has increased.

8. The system according to claim 7, wherein the control unit is configured to determine if the amount of the detectable substance in the combustion products has increased beyond a predetermined threshold; and wherein the control unit is configured to send a warning communication if the amount of the detectable substance in the combustion products has increased beyond the predetermined threshold.

9. The system according to claim 1, wherein the indicator coating comprises an adhesive;

wherein the adhesive of the indicator coating is configured to bind to the cold side of the combustion duct until a threshold temperature is achieved; and wherein the adhesive characteristics of the adhesive of the indicator coating is configured to degrade once the threshold temperature is achieved.

10. The system according to claim 9, wherein the indicator coating is configured such that degradation above the threshold temperature causes the coating to detach from the cold side of the combustion duct.

11. The system according to claim 1, wherein the gas sensor is disposed in a stack.

12. The system according to claim 1, wherein the detectable substance comprises a rare earth element.

13. The system according to claim 1, wherein the detectable substance comprises cadmium or magnesium.

14. The system according to claim 1, wherein the gas sensor comprises a chromatography analyzer.

15. A method for detecting defects in a combustion duct of a combustion system of a combustion turbine engine comprising a combustor which produces combustion products while the combustion turbine engine operates, wherein the combustion duct comprises a hot side, which is exposed to the combustion products and, opposing the hot side, a cold side, the method including the steps of:

coating the cold side of a transition piece of the combustion duct with an indicator coating, the indicator coating comprising a detectable substance;

positioning a gas sensor downstream of the combustor, the gas sensor configured to take a measurement of an amount of the detectable substance in the combustion products of the combustion turbine engine; and using the gas sensor to determine the amount of the detectable substance in the combustion products of the combustion turbine engine.

16. The method according to claim 15, wherein the indicator coating comprises a coating that degrades above a threshold temperature; and wherein the indicator coating is configured such that the degradation above the threshold temperature causes the indicator coating to detach from the cold side of the combustion duct and the detectable substance to enter the combustion products of the combustion turbine engine;

further comprising the step of determining if the amount of the detectable substance in the combustion products of the combustion turbine engine exceeds a predetermined threshold.

17. The method according to claim 16, wherein the indicator coating comprises an adhesive;

wherein the adhesive of the indicator coating is configured to bind to the cold side of the combustion duct until a threshold temperature is achieved; and wherein the adhesive characteristics of the adhesive of the indicator coating is configured to degrade once the threshold temperature is achieved.

18. The method according to claim 16, wherein the hot side comprises a protective coating; and wherein the threshold temperature corresponds to an elevated temperature that results from a defect in the protective coating of the hot side.

19. The method according to claim 18, wherein the defect comprises spallation of the protective coating from an area on the hot side, the area of spallation comprising at least a threshold size, wherein the threshold size corresponds to the size required to cause the threshold temperature at the cold side.

20. The method according to claim 18, wherein the combustion duct comprises one of a transition piece and a liner;

wherein the protective coating comprises a thermal barrier coating; and wherein the adhesive of the indicator coating comprises one of a ceramic adhesive, a ceramic putty, and an epoxy silicone.

21. The method according to claim 20, wherein the gas sensor is disposed in a stack; and wherein the detectable substance comprises a rare earth element.

22. The method according to claim 21, wherein the detectable substance comprises cadmium or magnesium; and wherein the gas sensor comprises a chromatography analyzer.

23. The method according to claim 16, further comprising the steps of:

taking and recording an initial measurement of the amount of the detectable substance in the combustion products of the combustion turbine engine;

taking and recording a subsequent measurement of the amount of the detectable substance in the combustion products of the combustion turbine engine; and comparing the initial measurement against the subsequent measurement to determine if the amount of the detectable substance in the combustion products has increased, and, if the amount of the detectable substance in the combustion products has increased, the rate of the increase.

24. The method according to claim 23, wherein the control unit is configured to determine if the rate of increase is greater than a predetermined threshold.

* * * * *